(12) United States Patent
Zhai et al.

(10) Patent No.: US 9,448,162 B2
(45) Date of Patent: Sep. 20, 2016

(54) TIME-RESOLVED SINGLE-PHOTON OR ULTRA-WEAK LIGHT MULTI-DIMENSIONAL IMAGING SPECTRUM SYSTEM AND METHOD

(75) Inventors: Guangjie Zhai, Beijing (CN); Wenkai Yu, Beijing (CN); Xuefeng Liu, Beijing (CN); Xuri Yao, Beijing (CN); Chao Wang, Beijing (CN); Zhibin Sun, Beijing (CN)

(73) Assignee: Center for Space Science and Applied Research, Chinese Academy of Sciences (CN)

( * ) Notice: Subject to any disclaimer, the term of this patent is extended or adjusted under 35 U.S.C. 154(b) by 239 days.

(21) Appl. No.: 14/351,028

(22) PCT Filed: May 14, 2012

(86) PCT No.: PCT/CN2012/075444
§ 371 (c)(1),
(2), (4) Date: Apr. 10, 2014

(87) PCT Pub. No.: WO2013/060134
PCT Pub. Date: May 2, 2013

(65) Prior Publication Data
US 2014/0253713 A1 Sep. 11, 2014

(30) Foreign Application Priority Data

Oct. 25, 2011 (CN) .......................... 2011 1 0328462
Oct. 26, 2011 (CN) .......................... 2011 1 0328748

(51) Int. Cl.
| | | |
|---|---|---|
| *G01N 21/25* | (2006.01) | |
| *G01N 21/64* | (2006.01) | |
| *G01N 21/17* | (2006.01) | |
| *H03K 21/38* | (2006.01) | |
| *G01J 1/04* | (2006.01) | |

(Continued)

(52) U.S. Cl.
CPC ........... *G01N 21/255* (2013.01); *G01J 1/0414* (2013.01); *G01J 1/4228* (2013.01);

(Continued)

(58) Field of Classification Search
CPC ............... G01N 21/255; G01N 21/17; G01N 21/6456; G01N 21/38; G01N 21/486
USPC .......................................................... 348/80
See application file for complete search history.

(56) References Cited

U.S. PATENT DOCUMENTS

2006/0239336 A1* 10/2006 Baraniuk ................ H04L 25/20
375/216
2013/0188854 A1* 7/2013 Bilgic .................... A61B 5/055
382/131

(Continued)

FOREIGN PATENT DOCUMENTS

| CN | 1737536 | 2/2006 |
|---|---|---|
| CN | 101387548 | 3/2009 |

(Continued)

*Primary Examiner* — Hee-Yong Kim
(74) *Attorney, Agent, or Firm* — Jack Schwartz & Associates, PLLC

(57) ABSTRACT

A single-photon or ultra-weak light multi-D imaging spectral system and method. In order to realize rough time resolution, a time-resolved single-photon counting 2D imaging system for forming color or grey imaging is provided. Moreover, in order to realize high-precision time resolution, the system comprises a light source, an imaging spectral measurement unit, an electric detection unit, a system control unit and an algorithm unit. The light carrying information of an object is imaged on a spatial light modulator and randomly modulated according to compressed sensing theory, emergent light of a grating is collected using a point or array single-photon detector, the number of photons and photon arrival time are recorded, and reconstruction is carried out using the compressed sensing algorithm and related algorithm of the spectral imaging. The system provides single-photon detection sensitivity, high time resolution and wide spectral range, and can be applied in numerous new high-tech industries.

12 Claims, 6 Drawing Sheets

(51) Int. Cl.
*G01J 1/42* (2006.01)
*G01S 17/89* (2006.01)
*G01S 7/481* (2006.01)
*G01S 7/486* (2006.01)
*G02B 26/08* (2006.01)

(52) U.S. Cl.
CPC ......... *G01N 21/17* (2013.01); *G01N 21/6456* (2013.01); *G01S 7/486* (2013.01); *G01S 7/4816* (2013.01); *G01S 17/89* (2013.01); *G02B 26/0833* (2013.01); *H03K 21/38* (2013.01)

(56) References Cited

U.S. PATENT DOCUMENTS

2013/0341487 A1 12/2013 Zhai et al.
2014/0043486 A1 2/2014 Zhai et al.

FOREIGN PATENT DOCUMENTS

| | | |
|---|---|---|
| CN | 101776760 | 7/2010 |
| CN | 102393248 | 3/2012 |

* cited by examiner

TIME-RESOLVED SINGLE-PHOTON OR ULTRA-WEAK LIGHT MULTI-DIMENSIONAL IMAGING SPECTRUM SYSTEM AND METHOD

FIELD OF THE INVENTION

The invention relates to the technical field of single-photon time-resolved imaging spectrum, in particular to a time-resolved single-photon or ultra-weak light multi-D spectral imaging system and a time-resolved single-photon or ultra-weak light multi-D spectral imaging method.

BACKGROUND OF THE INVENTION

The invention is an improvement and an innovation on the basis of previous work. In the field, the present research institute has already obtained two patents in China, namely Single-Photon Counting Imaging System and Method (application number or patent number: 201110103559.3, applicant or patentee: Center for Space Science and Applied Research, Chinese Academy of Sciences) and ULTRA-WEAK LIGHT MULTISPECTRAL IMAGING METHOD AND SYSTEM (application number or patent number: 201110166471.6, applicant or patentee: Center for Space Science and Applied Research, Chinese Academy of Sciences). Both of these two patents were based on the compressed sensing theory, the spatial light modulation technology and the single-photon detection technology and are used for single-photon counting imaging; and the difference between them lies in that the former realizes 2D imaging of an ultra-weak light object on single-photon level only by using a single-photon detector as a detection element, and the latter realizes ultra-weak light multispectral color imaging on single-photon level by using a single-photon counter linear array serving as a detection element together with a spectrophotometer. However, the two patents have the common defects: only static objects can be imaged but without light intensity analysis, time-resolved and spatial 3D resolution capacities; only algorithm simulation is performed without considering the influence of system noise, so the actual reconstruction precision is low; the problem of synchronism of a counting system and a digital mirror device (DMD) is not solved. Therefore, there still exist technical defects in these two patents. In order to solve the problems of time resolution and multi-D parameter detection and imaging, the present invention provides a time-resolved single-photon or ultra-weak light multi-D spectral imaging system and a time-resolved single-photon or ultra-weak light multi-D spectral imaging method for overcoming the above-mentioned drawbacks.

The so-called "time resolution" means to distinguish an interval on the dimension of time, and "ultrahigh time resolution" means to observe physical and chemical transient processes with the capacity of resolving the time of the processes. In a liquid phase, many physical and chemical processes such as cis-trans isomerism and orientation relaxation of molecules, transfer of charges and protons, collision pre-dissociation, energy transfer and fluorescence lifetime of excited molecules, and solvation of electrons in water can be completed in only $10^{-8}$ seconds, and it is possible to observe these extremely fast processes timely only through an analysis instrument with a time resolution precision of picoseconds. In the present invention, single-photon detection and counting sampling are expected to be carried out in large-scale or extremely short time intervals.

Moreover, currently the technologies for transient ultra-weak light (such as fluorescence lifetime) measurement mainly comprise the single-molecule detection technology, the time resolution technology and the super-resolution measurement technology, wherein: (1) the single-molecule detection technology mainly comprises wide field confocal fluorescence microscopy, scanning near field optical microscopy (SNOM), total internal reflection fluorescence (TIRF) microscopy, atomic force optical microscopy (AFOM) and Raman scattering technology; (2) the time resolution technology mainly comprises fluorescence lifetime imaging microscopy (FLIM), double-photon fluorescence lifetime microscopic imaging, fluorescence lifetime correlation spectroscopy (FCS) and multi-D fluorescence lifetime microscopy; and (3) the super-resolution measurement technology mainly comprises stimulated emission depletion (STED) microscopy, position sensitive microscopy (PALM, STORM, dSTORM and GSDIM), optical fluctuation (SOFI) microscopy and fluorescence resonance energy transfer (FRET) microscopy. According to a fluorescence lifetime imaging and related spectral quantitative measurement method for biological macromolecules, single-point fluorescence lifetime and related spectral measurement is carried out by an FLIM or FCS system, and then fluorescence lifetime imaging and related spectral quantitative measurement of the biological macromolecules is performed by adopting a laser beam scanning or sample scanning system. Because of the poor stability of nano displacement scanning platform and the complexity of the scanning process, not only is the manufacturing cost increased, but also the test time for nano materials and biological macromolecules is greatly prolonged and so the success rate is also significantly affected. According to a high-resolution microstructure imaging measurement method for a nano material, graphic representation is carried out generally by adopting an electron scanning microscope. Because the sample under measurement may be damaged by ionization of high-energy electrons, it is impossible to realize non-destructive imaging measurement of the bioactive molecules and the nano materials. The above technologies have such a common problem that spatial fluorescence lifetime measurement and related spectral analysis of an observed object cannot be carried out at the same time. With the development of scientific research towards high spatial resolution, high time resolution, multiband, fast detection, photon excitation and the like, it increasingly seems that the functions cannot meet the increasing requirements any more.

According to the global optical microscopy market analysis reports of Future Markets, Inc. in August 2011 and Global Industry Analysts, Inc. in February 2011, the annual profit of the global optical microscopy market is predicted to exceed 4.1 billion dollars until 2017. The demand for advanced, high-resolution and high-precision micro-imaging in current and future new markets is continually increased, and particularly the technical progresses in the fields of semiconductors, electronics, industry, micro electromechanical systems, biomedicine pharmacy, nano technology and nano material research and development greatly promote the increase of demand of related instruments. In brief, the time-resolved imaging spectrometry has attractive market development prospect, and can greatly promote the development of related industries. Basic scientific research of nano materials, crystal materials, nondestructive detection of the materials, quantum dot systems, photonic crystal, high-speed phenomenon detection, high-resolution spectrum measurement and quantum chemical basic science research in physical and chemical research as well as forefront problems of biophysical science of medical diagnosis, monomolecular biophysics, nano biological effect, molecular bionics, brain functions and recognition, proteomics and the like in biophysical research need the novel imaging system and method to realize the breakthrough of multi-disciplinary, multi-parameter and multi-scale quantitative research. A lot of research about life science, material science, chemistry and energy science indispensably needs to know components included in the investigated objects and changes of the components therein, and spectral imaging analysis is one of the most effective nondestructive analysis means for component analysis; the research requirement for where the components of the investigated object are distributed and how the components have changed, namely spatial distribution information of the changed components, can be realized by means of the spectral imaging analysis; with the development of scientific research, people not only need to know the spatial distribution information of the components, but also need to know the changing process of the components with time, particularly whether any intermediate product(s) being produced, the process of forming, annihilation and the acting mechanism of the intermediate products in the component change process, thus raising a requirement of time resolution for imaging spectrometry; and in order to achieve the following targets of determining the components, the quantity of each components, time resolved and location-determined of the components, two critical technical obstacles, namely the problems of dimensions and sensitivity, cannot be avoided no matter which solution is adopted. In the existing imaging spectrometry, the spectral imaging analysis of 1D spectrum or any dimension of spectrum of 2D planar images must be realized in an auxiliary scanning mode. This working mode brings the defects that the time duration for sampling must reserve sufficient time for scanning, and moreover, it is difficult to realize ultrahigh time resolution in the sense of electronics or the devices themselves because a planar sensor is composed of a large number of photosensitive detection units. Internationally, currently implemented solutions of instruments having time-resolved imaging spectrometry function can be divided into two types: scheme I, the function of 2D spatial scanning is added to a time-resolved spectrometer, but this scheme has the defects that its efficiency is low due to the time conflict between time resolution and spatial scanning and so its whole performance cannot meet higher scientific research requirements; and scheme II, the function of time resolution is added to an image spectrometer or an optical channel is added to a single-photon micro-imaging device, but this solution has the defects that its time resolution capability is difficult to improve and cannot meet the time requirement of time-resolved spectrum and so its application range is limited.

From the view of the analysis of optical signal intensity of a research object, introducing spatial resolution into the function of a spectrometer means the intensity of source signals which can be captured by an optical sensor is reduced, and further the requirement of time-resolved measurement means further reduction of the intensity of source signals. The lower the intensity of the source signal is, the lower the intensity of the fluorescence signals to be captured by a detector. The sensitivity of detectors is the key performance of the time-resolved imaging spectrometer, i.e., the higher the sensitivity of the detector is, the better the performance of the equipment. Single-photon detectors can detect the minimum optical energy, which is the detection limit of light, hence single-photon detection technology is the final pursuit of the time-resolved imaging spectrometer ever since.

Because of the above-mentioned restriction of principle and detection technologies, a time-resolved single-photon multi-D imaging system can be possibly realized in real sense only by new principles and new methods. The present invention realizes measurements with 2D spatial resolution by adopting the latest developed compressed sensing theory and combining modern mature technical conditions through a single-photon point detector, wherein one dimension of a 2D spatial distribution will be saved, and compared with a surface element detector, the single-photon point detector has more advantages in the aspects of detection sensitivity and wavelength range, that is to say, with the extremely high sensitivity, high flux measurement, high signal-to-noise ratio, wide wavelength range and low cost, single-photon counting imaging realized by using a point detector will certainly become an important development trend of future single-photon level imaging. Single-photon counting imaging is an ultra-weak light detection technology, wherein the light intensity distribution is represented by recording the counts of the photons and the probability of detection of the photons to reconstruct an image.

A linear array or array, Geiger mode single-photon detector can be used to realize imaging spectrometry, with a time resolution precision of picosecond, a spatial resolution of nano level and a detection sensitivity of single-photon detection level, so as to realize in real sense single-photon time-resolved imaging spectrometry, which is in nature different from traditional imaging spectrometry. Here, the imaging spectrometry is an important technology for acquiring and displaying precise spectral information, because a spectral image contains more information about the spectrum, and the multispectral imaging technology greatly overcomes the phenomenon of metamerism. Moreover, the single photon, as an ultra-weak light, is regarded as the minimum energy unit of light that cannot be divided further. The discrete photon pulse signal is the detectable limit, and generally detected by a single-photon detector. When a counting-type single-photon detector works in a saturation state, whose sensitivity being in a single-photon level, it obtains a photon density image by adopting a statistical method; and when the detector works in a sub-saturation state, then the amplitude of the electrical signals output by the detector varies with the changes of the number of detected photons, and so an ultra-weak light image is acquired via these electrical signals. Ultra-weak natural discrete signals are identified and extracted by adopting pulse discriminating technology and digital counting technology in the single-photon counting method, wherein the performance of the method is affected very little by those instable factors and is free of most influence of the thermal noise of the detectors, so the digital signal output through the method has a greatly improved signal-to-noise ratio.

Since the theoretical basis of the invention is the compressed sensing theory and the spatial light modulator technology, the compressed sensing theory and the spatial light modulator technology of the prior art will be described in details hereafter.

The compressed sensing principle is a brand-new mathematical theory proposed by Donoho, Tao, Candès et al., which can perfectly recover original signals in a randomly sampling mode with smaller number of the sampling (far fewer than the limit of Nyquist/Shannon sampling theorem) and has higher robustness. The principle is mainly divided into three steps: compressive sampling, sparse transform and algorithm reconstruction, wherein the compressive sampling is a process for mapping the signals under measurement from high-D signals to low-D ones; the sparse transform means to select a proper $\Psi$, so that x' obtained after the $\Psi$ transform of x is sparse, namely x can be sparsely represented under the $\Psi$ framework; and the algorithm reconstruction is a process for solving y=A$\Psi$x'+e under the condition that the observation data y, the measurement matrix A and the framework $\Psi$ are known, and finally, x is recovered according to $x=\Sigma_{i=1}^{N} x'_i \psi_i$.

The spatial light modulator (SLM for short) is a device capable of loading information to a 1D or 2D optical data field and performing optical information processing, to be more specific, it can change the amplitude or the intensity, the phase, the polarization state and the wavelength of the spatial light distribution or convert the incoherent light into the coherent light, under the control of electric driving signals or other signals changed with time. The most typical representative of the SLM is a digital micro-mirror device (DMD for short), which is the most precise optical switch in the world. The core of the DMD is a micro-mirror array (mainstream DMD consists of a 1,024×768 array, maximally up to 2,048×1,152) consisting of thousands of micro-mirrors arranged on hinges, of size 14 μm×14 μm (or 16 μm×16 μm) for each mirror and being able to switch on/off the light on one pixel. Each of the micro-mirrors is suspended and can be caused to incline to its two sides by about 10 to 12° (+12° and −12° are selected here) in an electrostatic form by performing electronic addressing to a storage unit under each micro-mirror with a binary array signal, and the two states being marked as 1 (corresponding to "on") and 0 (corresponding to "off"), respectively; and when the micro-mirrors do not work, they are in an "anchorage" state.

SUMMARY OF THE INVENTION

It is thus an object of the invention that in order to "find" and analyze the components included in a research object to determine the quantity of each component at specific location and at specific time and the movement rule of the components on nano scale and picosecond scale, solve the problems brought up by the multiple dimensions, and realize the spectral image measurement of objects with the capability of reflecting, scattering or transmitting, wherein the spectral measurement having 5D parameters: two spatial dimensions, light intensity, time resolution and spectral resolution on ultra-weak light single-photon level, by combining the point or array single-photon detection technology of visible light and near infrared light, the time-resolved measurement technology, the spatial light modulation technology, the compressed sensing theory, the single-photon counting imaging technology, the spectral imaging and the reconstruction algorithm technology, and then provide a time-resolved single-photon multi-D imaging system and a time-resolved single-photon multi-D imaging.

To realize the above purpose, the present invention provides a time-resolved single-photon counting 2D imaging system that can obtain imaging spectrum, obtained by enabling an ultra-weak light source triggered by a trigger to illuminate an object, with the time precision of second level, based on the compressed sensing principle, and the present system is further used for imaging the object that changed dynamically with time and for outputting continuous gray level video image frames arranged according to the time sequence. The present system comprises:

a trigger, an optical imaging system, a DMD micro-mirror array, an optical focusing and collecting system, a light attenuator, a single-photon counter, a drive control module and an optimization algorithm module.

The trigger is triggered by an ultra-weak light triggering source located at the front end thereof and its output end is connected with the input end of the drive control module. When the trigger is triggered, the drive control module outputs a drive control signal to trigger the DMD micro-mirror array and the single-photon counter connected with the output end of the drive control module to start working. Then the DMD micro-mirror array starts flipping and the single-photon counter simultaneously starts the photon counting. The light attenuator is used for attenuating the intensity of the light. The optical focusing and collecting system is used for focusing and collecting lights. The single-photon counter is used for performing single-photon counting of the light.

The output end of the single-photon counter is connected with one input end of the optimization algorithm module, i.e., the counting result of the single-photon counter is used as an input parameter of the optimization algorithm module, and the other end of the optimization algorithm module is connected with an output end of the drive control module for receiving a random measurement matrix stored by the drive control module in a selected area as the other input parameter of the optimization algorithm module. The optimization algorithm module reconstructs a sparse signal according to the input measurement result of the single-photon counter and the random measurement matrix, then inverses a photon density image, and after M intervals t, a series of time-resolved 2D gray image video frames in time sequence can be reconstructed.

The DMD micro-mirror array is a digital micro-mirror device.

Further, the other output end of the drive control module is connected with the input end of the DMD micro-mirror array for driving and controlling the turnover of the DMD micro-mirror array, as an implementing example, the drive control module drives and controls the turnover of the DMD micro-mirror array by downloading a pseudorandom measurement matrix, after a working area of the DMD micro-mirror array is selected, on the basis of the digital light processing (DLP) technology. The DMD micro-mirror array sends a synchronous signal to the single-photon counter during the its turnover to ensure the synchronization between the DMD micro-mirror array and the single-photon counter, namely each time the DMD micro-mirror array turns over, the single-photon counter accumulatively accumulates the number of the single photons during the time interval of the turnover; after the turnover of the DMD micro-mirror array is finished, the single-photon counter is reset to restart accumulating. All the counts and the random measurement matrix of the selected area are transmitted to the optimization algorithm module.

In the above technical solution, when the system is used for color imaging, the single-photon counter is replaced by a linear array of the single-photon counters, and a spectrophotometer is arranged on the light path between the linear array of single-photon counters and the optical focusing and collecting system.

In the above technical solution, both the optical imaging system and the optical focusing and collecting system adopt optical lenses to perform optical imaging and optical focusing, respectively; and after ultra-weak light passes through the optical imaging system, isometric or reduced or enlarged images can be obtained on the DMD micro-mirror array and adjusted according to actual demands.

In the above technical solution, the optical focusing and collecting system couples beams split by the spectrophotometer to a fiber by adopting fiber coupling technology, and collects the split light to the corresponding single-photon counter separately by using fiber coupling technology.

The spectrophotometer comprises a light collimating section, a light splitting section, an angle measurement section and a luminosity observation and measurement section, and the spectrophotometer is used for spectral analysis and measurement;

Preferably, the spectrophotometer is a prism spectrophotometer or a grating spectrophotometer.

On the above basis, the present invention is further extended to a time-resolved single-photon multi-D imaging system. The system excites the fluorescence of an object through laser pulses on the basis of the compressed sensing principle likewise to obtain light intensity distribution and imaging spectrum, realizes time resolution precision of up to picosecond level by using the time resolution strategy, and thus can detect transient periodic matters such as fluorescence lifetime and the like. The system comprises:

a light source, a spectral imaging measurement unit, an electric detection unit, a system control unit and a processing unit;

the light source emits laser pulse, under the triggering of a trigger pulse sent by the system control unit, to an object to be measured, so that the object emits fluorescence carrying the information of itself;

the imaging spectrum measurement unit is used for imaging the light carrying the information of the object to be measured on a spatial light modulator (SLM), the SLM is modulated by adopting random light and reflects the image thereon, and the reflected light is collimated by a light converging and collecting component arranged on a light path and then irradiated on the electric detection unit;

the electric detection unit is used for detecting the incident light according to the time resolution strategy, recording the number of photons of the incident light as well as the dimension information of arrival time of each photon;

the processing unit is used for realizing spectral image reconstruction of multi-parameter information according to the input photon number, the arrival time dimension information of the photons and the random light modulation matrix information of each time period, by using the compressed sensing and spectral imaging algorithm, and for outputting eight types of images;

the system control unit is used for enabling each component, namely sending driving signals to each unit to make them start the normal work, for realizing the synchronization between pulse triggering of the light source and photon counting, and for controlling the turnover of the micro-mirror array and the replacement of the random matrix on the micro-mirror array and performing corresponding adjustment before or after a transient period;

In the above technical solution, the spatial light modulator is loaded with a Bernoulli binary random matrix through a random number generator to realize the random light modulation of light; the time resolution strategy adopts a frame-by-frame measurement method for a non-periodically changed long-time sequence process; an optimized time resolution strategy is adopted for a transient process with periodic change characteristic, specifically, the period of the transient process is cut into a plurality of detection sub time periods, during each sub time period a point or array single-photon detector detects the object to be measured and records the number of the photons and the dimension information of arrival time of the photons, wherein each minimum time unit is used as a reconstruction object.

In the time-resolved single-photon multi-D imaging system, preferably the electric detection unit further comprises:

a random number generating unit, which is used for generating a random number for modulating the spatial light modulator (SLM), and moreover, the random number generating unit is used for processing a real random number by treating a random source in the nature as a random number source to acquire the random number and outputting the random number to the SLM;

a high-precision time interval measurement instrument, which is used for dividing the time duration of detection and recording the duration between two moments in a time coordinate system to obtain time dimension information, wherein the precision can be controlled on picosecond level;

a point or array single-photon detector, consisting of a plurality of avalanche diodes corresponding to different wavelengths and working in a Geiger mode, which is used for enabling some of the avalanche diodes as required, so as to detect those arriving photons in each frame in the non-periodically changed long-time sequence process and detect the arriving photons in a preset time period of each period in the transient periodic process and then output a pulse waveform, wherein the preset time period is a subset of the periodic duration;

a multi-channel counter, which is used for screening and accumulating the number of peaks of the pulse and recording the number of photons and the arrival time of the photon detected by each channel of the point or array single-photon detector;

a delayer, which is used for sending control signals for laser pulse in a certain transient period and sending enabling gate control signals to the point or array single-photon detector or the high-precision time measurement instrument or delaying the gate width rising edge for a certain time period for sending, the delayed time period capable of being used as a detection time sub period of the point and single-photon detector in the corresponding transient period, and the time resolution precision being 20 ps;

wherein the delayer can be replaced by a time length division module which is used for equally dividing the transient period into a plurality of sub periods, each sub period is used as a time unit for detection and counting of photons for the point or array single-photon detector and the multi-channel counter, wherein the time resolution precision is 50 ps; and alternatively, the time length division module or the delayer can also be replaced by a time/amplitude converter arranged in the multi-channel counter, wherein the time/amplitude converter is used for converting the arrival time of the photons into a voltage, recording the voltage in the corresponding channels, dividing the photon numbers according to the arrival time of the photons into several sections and then obtaining the photon numbers of each of the multiple sections within one period, wherein the time resolution precision is 5 ps.

The time-resolved single-photon multi-D imaging system also comprises a grating light splitting component arranged on a light path between the light converging and collecting component and the point or array single-photon detector. The grating light splitting component collimates incident light into collimated light by using a concave mirror before splitting the light, after which the grating light splitting component collimates the light of each wavelength by using a lens to converges the light to the avalanche diodes in corresponding channels thereby acquiring the dimension information about the spectrum, namely acquiring the light intensity information in each wavelength, the dimension information about the spectrum is used for reconstructing an image containing the wavelength parameters of the spectrum. Furthermore, the grating light splitting generates zero-order diffraction, primary diffraction, secondary diffraction . . . , wherein the zero-order diffraction obtains an original image, the diffraction of the other orders obtains spectrum, and the spectrum of the primary diffraction is the brightest, and the total light intensity wavelength distribution can be obtained by detecting the spectrum of the primary diffraction or detecting the spectrum of each ordered diffraction spectrum respectively and then using a grating diffraction formula;

wherein the point or array single-photon detector is arranged on the focal plane of the grating light splitting component.

In the above technical solution, preferably, the processing unit further comprises:

a data read/write memory, which is used for storing each input sub time period, the number of photons in each frame or each enabling gate control signal time period, the dimension information of arrival time of each photon, the corresponding random matrix and the wavelength information corresponding to each channel of the detector, thus playing a role of data reading/writing and caching;

an algorithm processing unit, which is used for reconstructing images on the basis of the input counting values of the multi-channel counter, the random matrix for controlling a spatial light modulator-demodulator, the time dimension information recorded by the delayer or the time length division module or the time/amplitude converter, and the wavelength information corresponding to each channel of the detector, and then outputting the following eight types of images:

(1) when a single-phone 2D image I (x, y) is to be output, the algorithm processing unit reconstruct the image according to the input counting value and the random matrix parameters by adopting different sparse frameworks for different types of images and adopting the compressed sensing algorithm, and performs post processing on the image by combining the matrix completion theory, wherein the compressed sensing algorithm includes greedy reconstruction algorithm, matching pursuit (MP) algorithm, orthogonal matching pursuit (OMP) algorithm, base pursuit (BP) algorithm, LASSO, LARS, GPSR, Bayesian estimation algorithm, magic, IST, TV, StOMP, CoSaMP, LBI, SP, 11_ls smp algorithm, SpaRSA algorithm, TwIST algorithm, $l_0$ reconstruction algorithm, $l_1$ reconstruction algorithm, $l_2$ reconstruction algorithm and the like;

(2) when a single-photon 2D spectral image I (x, y, λ) is to be output, the algorithm processing unit is further provided with the wavelength information corresponding to each channel of the detector on the basis of (1) to obtain a light intensity spatial distribution image in each wavelength for an imaging spectrometer, and color imaging can be realized by using the light intensity spatial distribution under three primary colors, namely red, green and blue;

(3) when a single-photon time-resolved 2D image (such as fluorescence lifetime) I (x, y, t) is to be output, the algorithm processing unit is further provided with the dimension information of arrival time of the photons on the basis of (1), so as to reconstruct the image of an object in each sub period, thereby recovering the dynamic changing process of the image within the full time length;

(4) when a single-photon time-resolved 2D spectral image I (x, y, λ, t) is to be output, the algorithm processing unit is further provided with the dimension information of arrival time of the photons on the basis of (2), so as to reconstruct the image of the object in each wavelength of the light within each sub period;

(5) when a single-photon 3D image I (x, y, z) is to be output, for an object with large-scale time sequence and without exciting fluorescence, the algorithm processing unit further calculates the optical path difference of spatial positions, namely spatial third-dimensional distance information, by using the interval between the arrival time of the photons on the basis of (3), the optical path difference is a derivative and a subset of time-resolved dimension, thereby obtaining a plurality of layers of image frames corresponding to different spatial distances;

(6) when a single-photon 3D spectral image I (x, y, z, λ) is to be output, the algorithm processing unit is further provided with the wavelength information corresponding to each channel of the detector on the basis of (5) to obtain light intensity spatial 3D distribution in each wavelength;

(7) when a single-photon time solved 3D image I (x, y, z, t) is to be output, the algorithm processing unit identifies and distinguishes the large-scale spatial third-dimensional distance information and the dimension information of the sub periods of a transient period on the basis of (5), so as to reconstruct the time-resolved 3D image of the object, wherein the time length of the former is greater than that of the latter;

(8) when a single-photon time-resolved 3D spectral image I (x, y, z, λ, t) is to be output, the algorithm processing unit identifies and distinguishes the large-scale spatial third-dimensional distance information and the dimension information of the sub periods of a transient period on the basis of (6), so as to obtain a time-resolved 3D spectral image.

The compressed sensing principle is mainly divided into three steps: compressive sampling, sparse transform and algorithm reconstruction, wherein the compressive sampling is a process for mapping measured signals from high-D signals to low-D ones; the sparse transform is a process for selecting a proper sparse framework; and the algorithm reconstruction is a process for recovering signals under the condition that the observation data y, the measurement matrix A and the framework Ψ are known.

According to the compressed sensing theory, a micromirror array is required to perform random reflection on light carrying the compressible observation object information. When a single micro-mirror in the micro-mirror array turns over +12°, the reflected light is received by the point or array single-photon detector; when a single micro-mirror in the micro-mirror array turns over −12°, the reflected light cannot be received by the point or array single-photon detector, by which the compressive sampling of the measured signals is completed, meanwhile, real randomness of bright and dark matrix of the micro-mirror array is ensured, and then the probability of reflecting the ultra-weak light to the light converging and collecting component is controlled to be random.

Mathematical models of the compressed sensing theory are as follows:

If $x \in R^N$ is the data to be measured, $y \in R^M$ is the observation data, $A \in R^{M \times N}$ is a random projection matrix (M☐N) and $e \in R^M$ is system noise, assume K is the number of nonzero elements in x, also called sparsity, then the compressive sampling process can be described as formula (1):

$$y = Ax + e \qquad (1)$$

If x is compressive or can be sparsely represented, then $x = \sum_{i=1}^{N} x'_i \psi_i$, wherein $\Psi = [\psi_1, \psi_2, \ldots, \psi_N]$ is a sparse transform matrix, then formula (1) is transformed into formula (2):

$$y = A\Psi x' + e \quad (2)$$

wherein $A\Psi$ meets the RIP criterion; the more irrelevant between A and $\Psi$ is, the smaller the value of the measurement times M required by the sampling process is, and the smaller the calculation quantity is. In the invention, in formula (2), $\Psi$ is a framework, and A is a random measurement matrix.

If the number of the pixels in the 2D image is N, then the measurement matrix in formula (1) is $A = [a_1; a_2; \ldots; a_N]$, and $a_i$ is the $i^{th}$ row of A. The columns of the 2D images of the p×q pixels are connected end to end to form an N×1 (wherein N=p×q) 1D column vector, and corresponding to x in formula (1), each element of the vector represents the photon intensity at the corresponding position. The rows of the micro-mirror array during every turnover are connected end to end to form a 1×N 1D row vector, and corresponding to a row in the measurement matrix A, each element of the vector represents whether the micro-mirror at the corresponding position turns over to the principal axis of the light converging and collecting component or not, and the measurement matrix A totally has M dimensions, namely is a matrix with M rows and N columns.

The micro-mirror array starts the random turnover under the control of the system control unit, each time the number of the photons detected by the point or array single-photon detector is written as n, which is equivalent to the inner product value of the photon intensity image and the random measurement array of the micro-mirror array, and corresponding to an element of the observation vector y in formula $$y_i = \sum_{j=1}^{n} A_{i,j} x_j. \quad (1)$$

The whole group of observation data y (y is a M×1 1D column vector) can be obtained by repeating M times of measurements.

The sparse reconstruction means to solve x in formula (1) under the condition that the observation data y and the measurement matrix A are known, which is an ill-posed problem and generally solved by using the compressed sensing algorithm, wherein the algorithm can be divided into multiple types as mentioned above, as an example, a common expression mode is selected, and the algorithm is described as formula (3):

$$\min_{x'} \frac{1}{2} \|y - A\Psi x'\|_2^2 + \tau \|x'\|_1 \quad (3)$$

wherein $\| \ldots \|_p$ represents a norm operator, $(\|x\|_p)^p = \sum_{i=1}^{N} |x_i|^p$, the first item is a least-square constraint marked as f(x); the second item is a constraint for the sparsity of x; and the sum of the two items is a target function. The original signals can be perfectly reconstructed by only $M \leq O(K \cdot \log(N/K))$ times of measurements.

The abovementioned technical solution is used for reconstructing the image of monochromatic light according to the light intensity dimension information; if the spectral dimension information is also considered, then the signals of each wavelength are reconstructed respectively, and also spectrum analysis can be carried out; if the time dimension information is also considered, then the signals are reconstructed within time intervals according to the time-resolved measurement method on the basis of the above mentioned, and so time resolution can be realized. The arrival time of the photons acquired in the time resolution can be transformed into the dimension information of spatial distance under certain conditions, namely the signals are classified according to the distance from the detection location, and the algorithm is used for reconstructing a plane image of each distance and finally superposing the reconstructed images of each of the distances together to form a spatial 3D image.

The invention also provides a time-resolved single-photon multi-D imaging method. The method is based on the above system and comprises the following processes:

imaging the light released, reflected, scattered, transmitted or refracted from an object by being excited or self-exciting on a spatial light modulator through a lens set under the condition of ultra-weak light single photons;

setting a random modulation base on the spatial light modulator according to the compressed sensing theory, collecting the reflected light of the spatial light modulator to a point or array single-photon detector; implementing reconstruction of spectral image with 5D parameters information by adopting the time-resolved strategy through the compressed sensing algorithm and the spectral imaging algorithm, thus finally realizing the single-photon time-resolved spectral image on nano scale and picosecond scale;

wherein the time-resolved measurement strategy can adopt any one of the following three methods:

Strategy I: The period of the transient process is 1.5 ms to 5 ms. A light source is turned on. Here, the transient period is marked as T, when T is equally divided into the number of d time intervals, those intervals are marked as $t_1$, $t_2$, $t_3$, ..., $t_d$ respectively. During T, the random modulation base matrix on the spatial light modulator is kept constant. A point or array single-photon detector detects the single photons within the time interval $t_i$, respectively, wherein i=1, 2, ..., d, and a multi-channel counter records the number of the single photons within each time interval, said counts of single photons are combined with the time codes recorded by a high-precision time measurement instrument to form a data packet, thus obtaining the time interval corresponding to each count. Before the next laser pulse is emitted, namely at the moment when the sampling of d time intervals of period T is just finished, the spatial light modulator instantly turns over to the next frame to carry out the whole set of operations as above. The spatial light modulator repeats the turnovers for P (1≤P<N) times so that each time interval $t_i$ has corresponding a number of P counts corresponding to P random matrices, respectively. By performing algorithm reconstruction on these d time intervals, respectively, according to the one-to-one correspondence relationship, the changing process of the spectral intensity within a transient period can be retrieved. If the light intensity is ultra-weak, by performing multiple times of measurement and accumulation, the corresponding counts are increased, and then by performing algorithm reconstruction on the d time intervals, respectively, according to the one-to-one correspondence relationship, the changing process of the spectral intensity within a transient period can be retrieved;

Strategy II: The period of the transient process is 80 ns to 1.5 ms. At the same time when a trigger pulse is sent to a light source, an enabling control signal is also sent to each component of the system, wherein the enabling control signal passes through a delayer before arriving at the point or array single-photon detector and the high-precision time measurement instrument. To be more specific, 1) keeping a fixed frame of the spatial light modulator unchanged, keeping the start end of the gate width of the point or array single-photon detector being coincides with the starting moment of the transient period, the point or array single-photon detector and the high-precision time measurement instrument simultaneously start the measurements and only make the measurement once within the period T, wherein the gate width is smaller than the transient period T, to obtain a counted number which is the number of the single photons in the overlapping time period of the gate width and the transient period. By repeating the above procedure 1) for Q times and summing up the counts of every time of the Q times repeated the measurements, thereby a first sum is obtained. Then the gate width is increased by 20 ps by using a digital delayer. By performing the above procedure 1) for Q times, a second sum is obtained. The first sum is regarded as a reference value and the difference between the first sum and the second sum is regarded as the statistic counted number within the delayed gate width. Through this way, the statistical counted number of d sections from the reference moment to the end moment of the fluorescence light is obtained; 2) in addition, if the gate width is kept unchanged but the arrival moment of the gate width is shifted to an earlier moment, similarly, a series of statistical counted numbers of d sections between the fluorescence lifetime starting moment and the reference moment could be obtained. Next, the spatial light modulator is turned over once to carry out the whole set of operation as above; repeating P times of turnover of the spatial light modulator so that each time interval $t_i$ has corresponding P counted numbers corresponding to P random matrixes, respectively. Based on the one-to-one correspondence relationship between the P counts and the P random matrixes, it is possible to reconstruct the transient process of an image within a period by performing algorithm-based reconstruction on the d time intervals. If the light intensity is ultra-weak, multiple times of measurements and accumulations are performed so that the corresponding counts are increased;

Strategy III: keeping a fixed frame of the spatial light modulator unchanged, taking the trigger pulse sent to the light source as a reference pulse of a time to amplitude converter, then the time to amplitude recording the arrival time of the photons in form of voltage into a corresponding time channel; dividing the photon numbers into multiple sections according to the arrival time of the photons, then a series of statistical counts of d sections within one period could be obtained. Next, the spatial light modulator is turned over once to carry out the whole set of operation as above; repeating P times of turnover of the spatial light modulator so that each time interval $t_i$ has corresponding P counts corresponding to P random matrixes respectively. Based on the one-to-one correspondence relationship between the P counts and the P random matrixes it is possible to reconstruct the transient process of an image within a period by performing algorithm-based reconstruction on the d time intervals. If the light intensity is ultra-weak, multiple times of measurements and accumulations are performed so that the corresponding counted numbers are increased.

In the above technical solution, the spatial light modulator is a micro-mirror array;

the single-photon detector can be a photoelectric multiplier, an intensified charge coupled device (ICCD), an electron multiplying charge coupled device (EMCCD) or a linear mode or Geiger mode single-photon detector;

the light source emits infrared or visible light, and the laser is a femtosecond or nanosecond pulse laser with proper wavelength.

In the technical solution, collecting and detecting components are simultaneously arranged on the positive light path and the negative light path of the spatial light modulator, for performing coincident measurements. The quality of the reconstructed images can be improved and the operating time of the recovery algorithm can be shortened by using the co-relationship between the positive random measurement matrix and the negative random measurement matrix and adopting associated recovery algorithm.

In summary, according to the single-photon time-resolved spectral imaging method, the single-photon counting compressed sensing imaging technology is introduced into the fluorescence lifetime imaging (FLIM) system. The present international fluorescence lifetime imaging and fluorescence spectral imaging systems generally adopt the high-precision light detection technology of the photoelectric multiplier, the ICCD, the EMCCD and the like. The invention combines the compressed sensing theory, the single-photon detection technology and the fluorescence lifetime measurement technology for the first time, wherein considering the influence of the scanning mode on the stability of fluorescence lifetime imaging, the ultra-weak light image is mapped to the random micro-mirror array, the reflected light of the ultra-weak light from the micro-mirror array is converged to the point or array single-photon detector; the number of the photons is counted section by section, the subsection counted number sequence is calculated in a compressed sensing mode to reconstruct an image, thus single-photon time-resolved spectral image with 5D parameters can be acquired at the same time.

Compared with the prior art, the invention has the advantages that the system realizes spectral imaging measurement with 5D parameter information of two spatial dimensions with nano precision, light intensity, time resolution with picosecond precision and spectral resolution by the combination of the point and array single-photon detection technology of visible light and near infrared light, the time-resolved measurement technology, the spatial light modulation technology, the compressed sensing theory, the single-photon counting imaging technology, the imaging spectrometry and the reconstruction algorithm technology.

The main technical difficulty and the innovation of the invention comprise:

(1) The acquired single-photon counting data are grouped according to the time by using the point and array single-photon detection technology of the visible light and the near infrared light, and the groups are reconstructed by using the compressed sensing theory to realize single-photon time-resolved imaging.

(2) The single-photon counting data are grouped and calculated according to the time and the spectral section by using the point and array single-photon detection technology of the visible light and the near infrared light and the imaging spectrometry respectively to realize single-photon time-resolved spectral imaging, wherein the images and the spectrums can be measured at the same time.

(3) Because the spatial distance dimension is a subset of the time-resolved dimension, the spatial third dimension information can be acquired by using the spatial distance optical path difference calculated from the photon arrival time acquired by time resolution to realize 3D imaging, the longitudinal resolution reaches millimeter level, and the plane resolution can reach nano level.

(4) Proposed are three brand-new time-resolved measurement methods on the basis of the compressed sensing principle for the measurement of the transient period object, namely a time resolution method on the basis of time interval measurement, a time resolution method on the basis of delay measurement and a time resolution method on the basis of photon arrival time, so that the time resolution precision reaches picosecond level.

(5) The image quality is improved by selecting a proper framework and introducing the thought of matrix filling on the basis of compressed sensing.

(6) Corresponding algorithms are designed for 8 images by the combination of the compressed sensing theory.

On the basis of the advantages and the innovation, the system researched by the invention can be widely applied in the areas of numerous new high-tech industries such as monomolecular biophysics, material defect detection, nano materials, microelectronics, quantum dots, life sciences and new energy photoelectric conversion materials.

REFERENCE SIGNS

Figure 1:
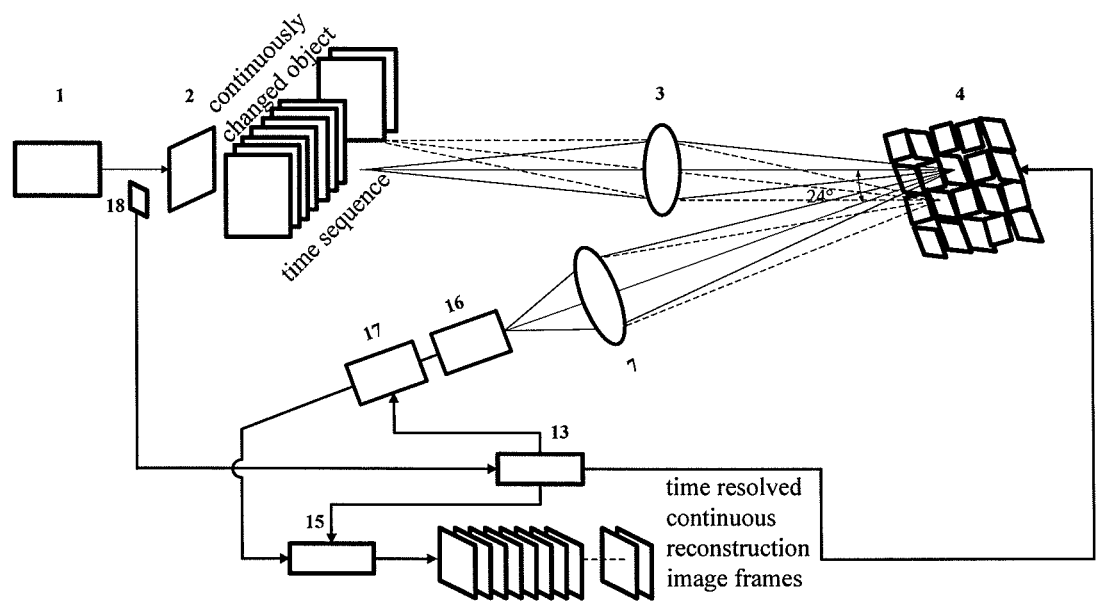
FIG. 1 is a structural schematic diagram of a time-resolved single-photon counting 2D imaging system of the invention.

I, light source
II, spectral imaging measurement unit
III, electric detection unit
IV, system control unit
V, algorithm unit
1, laser or halogen lamp with different wavelengths
2, light filter and attenuation plate
3, optical imaging component
4, spatial light modulator (SLM) or DMD
5, concave mirror (optional)
6, grating light splitting component
7, light converging and collecting component
8, random number generator
9, point or array single-photon detector
10, multi-channel counter
11, high-precision time measurement instrument
12, digital delayer (optional)
13, system control platform
14, data packet memory
15, compressed sensing and related algorithm
16, single-photon detector
17, counter
18, trigger
19, spectrophotometer
20, single-photon detector linear array

DETAILED DESCRIPTION OF THE EMBODIMENTS

The invention will be further illustrated in detail in conjunction with the drawings and the embodiments.

A time-resolved single-photon counting 2D imaging system provided by the invention features in that the system realizes time resolution of the ultra-weak light 2D imaging on single-photon level by combining the technology of trigger, compressed sensing, spatial light modulating technology, fiber coupling technology and the technology of detecting single photons, under the condition where the light is of large-scaled time and in the level of ultra-weak light single photon, wherein image signals are randomly projected through the technology of spatial light modulating to be transformed into random light intensity signals, which can be detected by single photon detector. After the triggering action of a trigger, the system starts to detect the single photons of the light and count the number of the single photons. At every time interval of t (t being on the order of seconds), a set of data (which corresponds to an image) are sampled, and the accumulated counts being treated as the measurement values. Finally, the image is reconstructed using the compressed sensing theory and related algorithm. As can be seen, the present system firstly concentrates on data sampling and then makes the calculation to reconstruct the image, with the advantages that the dynamic changes of an object to be measured can be observed in large-scale time by using a point detector.

Figure 2:
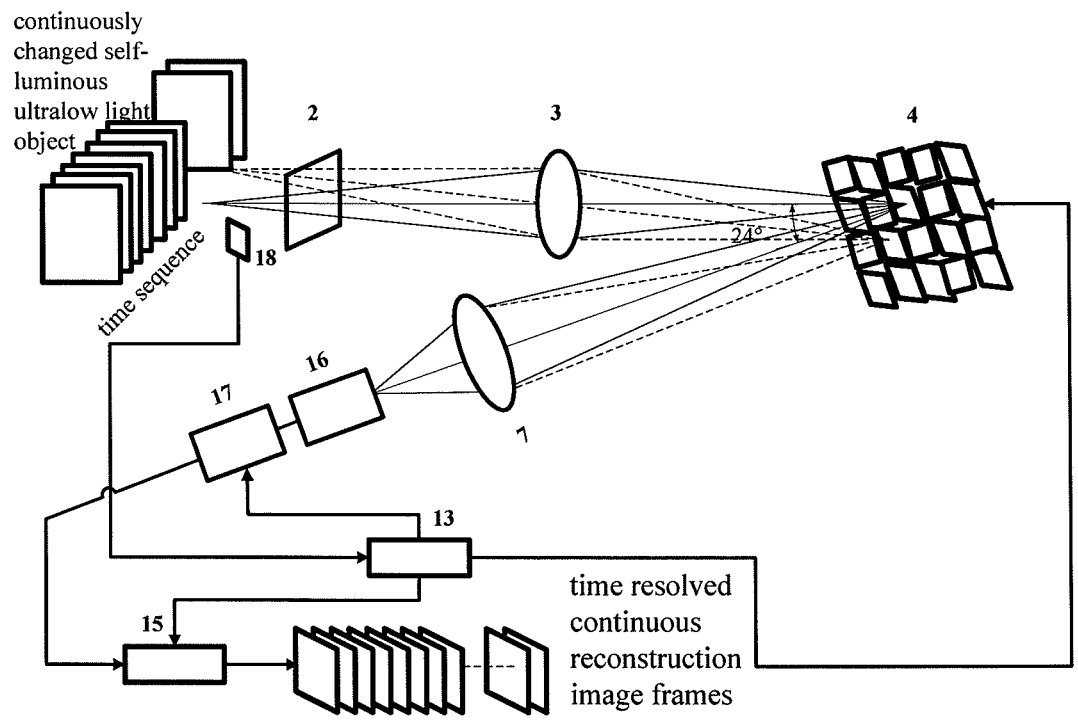
FIG. 2 is a structural schematic diagram of a time-resolved single-photon counting 2D imaging system of the invention when an observation object is a self-luminous object.

As shown in FIG. 1 and FIG. 2, the time-resolved single-photon counting 2D imaging system mainly comprises a laser or halogen lamp 1 with different wavelengths, a trigger 18, a light filter and an attenuation plate 2, an optical imaging component 3, a digital mirror device (DMD) 4, a light converging and collecting component 7, a single-photon detector 16, a counter 17, a system control platform 13 and a compressed sensing and an algorithm section 15.

Firstly, the single-photon detector 16 is enabled to lead continuous detection of single photons. The trigger 18 is connected with the system control platform 13, and starts to send the triggering pulse to the system control platform 13 when being irradiated by ultra-weak light to inform the system control platform 13 to send the drive control signal to drive the spatial light modulator (SLM) 4 to operate, and then counter 17 starts counting the number of single photons.

Another feature of the invention is the light filter used for filtering the parasitic light from the ultra-weak light, so that the ultra-weak light entering the subsequent components of the system fall within the wavelength range required by the detector. Meanwhile, if there are no limits of the wavelengths, the light filter can be omitted. Another feature of the invention is the attenuator, which is used for attenuating the light to the working range of the single-photon detector to prevent the saturation of the detector caused by over high light intensity or over-long gate control time of the single-photon detector 16. If the light intensity of the light source is extremely weak, the attenuator is not required. If the attenuator is placed after the light source, the light source can be changed into an ultra-weak light source, which will lead the system noise increased, so the position of the attenuation plate should be chosen carefully.

The spatial light modulator (SLM) 4 can turn over +12° and −12° (the SLM 4 of other model can turn over +10° and −10°. In the present system, +12° is set as a reflection angle that can be received, whereas the reflected light after being turned over by −12° can hardly enters the single-photon detector 16 and thus can be ignored, so the angle between the primary optical axis of the light converging and collecting component 7 and the primary optical axis of the optical imaging component is 24°. After the working region of the SLM 4 being selected, a random number file of the region is generated and downloaded in the system control platform 13, wherein the random number file is used to control the random turnover of the SLM 4. At the same time when SLM 4 turns over, it also sends a synchronous signal to the counter, so that synchronization between the SLM 4 and the single-photon detector 16 is ensured, namely each time SLM 4 turns over, the single-photon detector 16 accumulatively counts the number of the single photons within the time interval of the turnover. After the SLM 4 ends its turnover, the counter is reset to restart the accumulative counting. All the counted numbers are transmitted to the compressed sensing and related algorithm 15 through a data wire to be used in calculation together with random matrix later.

A further feature of the invention lies in that both the optical imaging component 4 and the light converging and collecting component 7 are in the form of optical lenses in charge of the optical imaging and the optical focusing, respectively, instead of a single lens used in previous techniques, which makes the application range of the invention wider. The maximum imaging area on the SLM 4 can reach 2,048×1,152 pixels. As is different from the prior art, after the ultra-weak light passes through the optical imaging component 4, isometric or reduced or enlarged images can be obtained on the SLM 4 according to actual demands. The subsequent light path collection relates to fiber coupling technology, wherein focused beams are coupled into a fiber. The innovative point of the invention is that the focused light is collected to the single-photon detector 16 by using fiber coupling technology, wherein the performance of the coupling technology directly affects the imaging performance, so coupling adjustment becomes more difficult.

A time-resolved single-photon counting 2D imaging system features in that only a gray image of the object can be acquired. If a single-photon detector linear array 20 is used to replace the single-photon detector 16, a color image of the object can be recovered by using the light intensity distribution of three primary colors, namely red, green and blue, furthermore, if a spectrophotometer is arranged on the light path between the single-photon detector linear array 20 and the light converging and collecting component 7, then the system can be extended to a time-resolved ultra-weak light multispectral imaging system.

Figure 3:
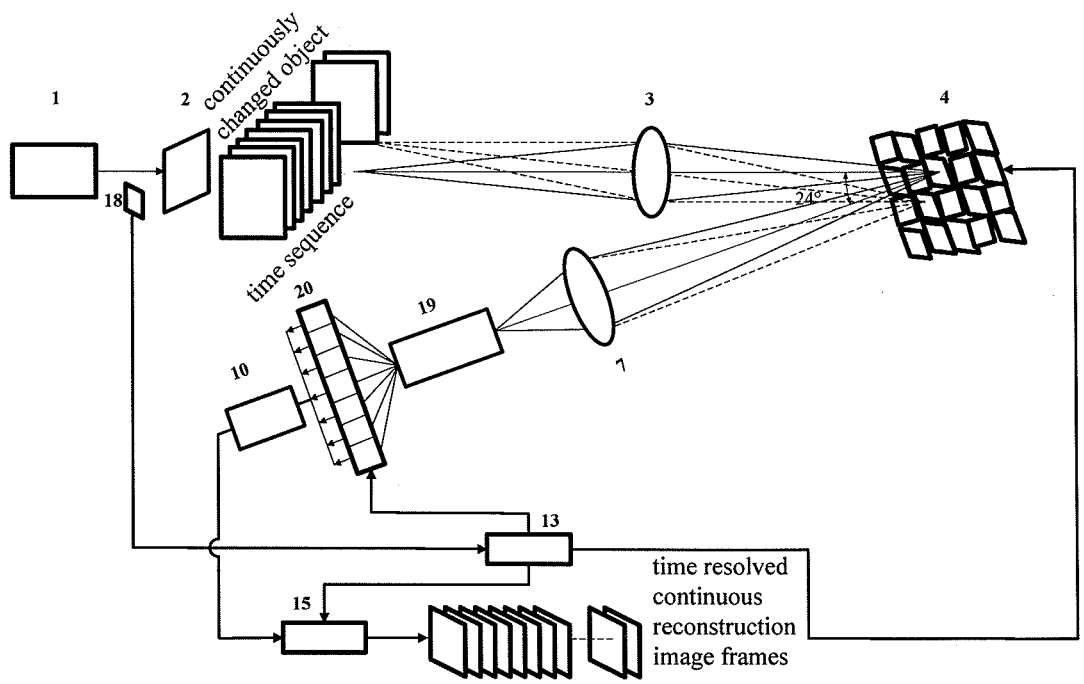
FIG. 3 is a structural schematic diagram of a time-resolved ultra-weak light multispectral imaging system on the basis of the compressed sensing theory in the invention.

As shown in FIG. 3, the invention also provides a time-resolved ultra-weak light multispectral imaging system, which comprises: a laser or halogen lamp 1 with different wavelengths, a trigger 18, a light filter and an attenuation plate 2, an optical imaging component 3, a DMD 4, a light converging and collecting component 7, a spectrophotometer 19, a single-photon detector linear array 20, a multi-channel counter 10, a system control platform 13 and a compressed sensing and related algorithm section 15, wherein the single-photon detector linear array 20 consists of a plurality of single-photon counters used for different wavelengths.

In the time-resolved ultra-weak light multispectral imaging system, the light converging and collecting component 7 is used for collecting and converging the light of different wavelengths contained in the spectrum to one corresponding channel of the single-photon detectors in the mode of free spatial coupling or a fiber collimating, wherein the fiber collimating mode is a priority selection for the single-photon point detector, and the free spatial coupling mode is priority selection for avalanche diode array.

Also, in the time-resolved ultra-weak light multispectral imaging system, the spectrophotometer 19 comprising a light collimating section, a light splitting section, an angle measurement section and a luminosity observation and measurement section, is used for spectrum analysis and measurement, wherein the spectrophotometer is a prism spectrophotometer or a grating spectrophotometer, or the light splitting of the spectrum can also be carried out using a light filtering wheel.

Figure 4:
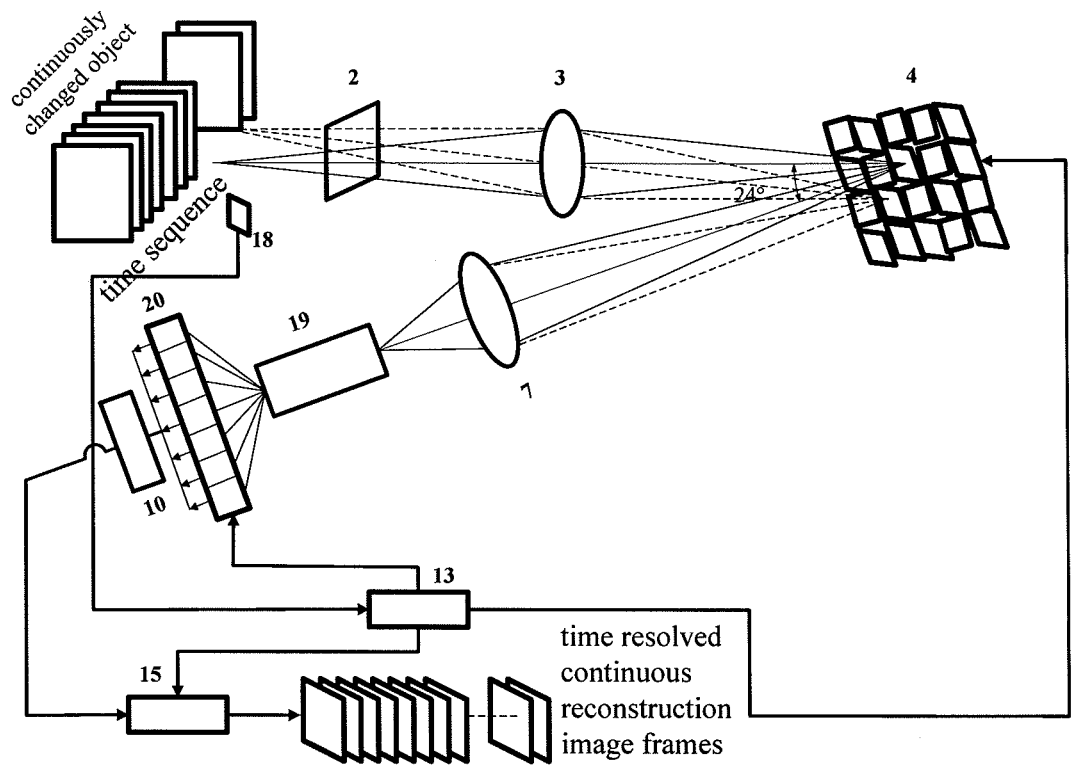
FIG. 4 is a structural schematic diagram of a time-resolved ultra-weak light multispectral imaging system of the invention when an observation object is a self-luminous object.

In the above two systems, the ultra-weak light is emitted from the object mainly through release, reflection, scattering, transmission or refraction after being illuminated onto the object being excited or self-exciting. As an alternative, when the observation object is a self-luminous object, the ultra-weak light source, namely the laser or halogen lamp 1 with different wavelengths can be removed from the time-resolved single-photon counting 2D imaging system, and the trigger 18 and the light filter and the attenuation plate 2 are moved to the light path on the right side of the self-luminous object, as shown in FIG. 2 and FIG. 4.

In the above two systems, two time resolution methods are introduced into the prior art, the methods are time resolution of a 2D plane image frame and time resolution of a plane image frame with spectrum dimension, respectively. Both methods adopt a frame-by-frame measurement mode, but the methods can only be used for imaging of dynamic object in large-scaled time of second-level, so the time resolution precision is relatively rough. However, many physical and chemical processes such as directional relaxation of molecules, transfer of charges and protons, collision pre-dissociation, energy transfer and fluorescence lifetime of excited molecules and solvation of electrons in water, can be completed in only $10^{-8}$ seconds, so in order to observe these extremely fast processes, an analysis instrument with a time resolution precision of picosecond is needed.

Figure 5:
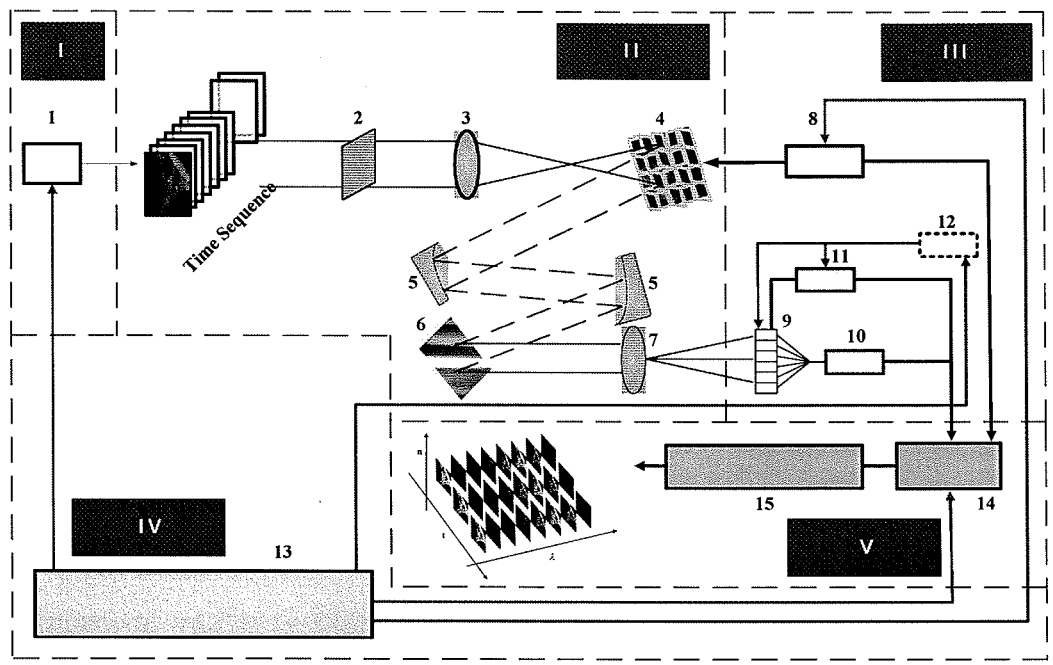
FIG. 5 is an overall structural diagram of a time-resolved single-photon multi-D imaging system provided in the invention.

As shown in FIG. 5, in order to solve the problem of high-precision time resolution, the invention also provides a time-resolved single-photon multi-D imaging system on the basis of the compressed sensing principle. The system excites the fluorescence of object by a laser pulse to obtain light intensity distribution and spectral imaging of the fluorescence, with a picosecond-level time resolution precision by using the time resolution strategy, and thus the system can be used to detect transient periodic matters with fluorescence lifetime and the like. The multiple dimensions comprise five dimensions, namely light intensity dimension, two plane dimensions, spectrum dimension and time dimension. The system comprises: a light source, a spectral imaging measurement unit, an electric detection unit, a system control unit and a processing unit.

The present invention is realized mainly based on the point and array single-photon detection technology of visible light and near infrared light, the time-resolved measurement technology, the spatial light modulation technology, the compressed sensing theory, the single-photon counting imaging technology, the imaging spectrometry and the reconstruction algorithm technology. The system comprises 5 units, namely a light source I, a spectral imaging measurement unit II, an electric detection unit III, a system control unit IV and an algorithm unit V.

The overall structural diagram of the time-resolved single-photon multi-D imaging system is shown in FIG. 5, the light emitted by a laser or halogen lamp 1 with different wavelengths is irradiated onto the observation object with a time sequence and enters into an optical imaging component 3 through a light filter and an attenuator 2, wherein a special light filter is used to filter out the parasitic light from the light and a monochromatic light filter is used to selectively enable the light in certain wavelengths to pass through. Moreover, when the light intensity of the source is relatively high, several groups of attenuation plates can be used for light attenuation, so that the light reaches single-photon level to prevent saturation of the following arranged point or array single-photon detector 9. The image of the observation object is imaged on the spatial light modulator (SLM) 4 by the optical imaging component 3, and the SLM 4 is used for randomly modulating the light through loading a random number generated by a random number generator 8, so that the emergent light from the SLM 4 deflects to the direction of the subsequently arranged light converging and collecting component 7 randomly within a certain range of probability. According to the compressed sensing theory, the higher the randomness of the light being deflected to the direction of the light converging and collecting component 7 is, the higher the imaging performance is. The light can be converged and collected in multiple modes, in order to make the stray light be able to be received by the point or array single-photon detector 9. It shall be noted that the light converging and collecting path drawn in FIG. 5 is only used for illustration rather than a unique evaluation criterion. In order to implement spectrum detection, a grating light splitting component 6 is also required for measurement of optical signals with spectral resolution, and each single-photon point detector in the point or array single-photon detector 9 is used for capturing the light of each specific wavelength.

As a supplement of the technical solution, according to the different light splitting mechanisms of spectrum, generally the light can be split in a filtering mode or a dispersion mode. For the light splitting in filtering mode, the light in a preset certain spectrum range can be detected, and be "scanned" in the dimension of spectrum by rotating a filter wheel and the like. For the light splitting in dispersion mode, a dispersion element (a prism or a grating) projects the light fields of different wavelengths reflected by the spatial light modulator (SLM) 4 to different positions of the point or array single-photon detector 9 sequentially from a short wavelength to a long wavelength, so that the scanning is not required and images of all spectrum ranges are simultaneously obtained. Moreover, in this light splitting mode, the spectrum resolution is in direct proportion to the parallelism of the incident light reaching the dispersion element (the prism or the grating), namely the better the parallelism is, the higher the spectral resolution is, where in fact the spectral resolution and the space resolution restrict mutually. As an example for explanation, a blazed grating may be used for the light splitting of the spectrum in dispersion mode. The light field reflected by the SLM 4 is collimated and projected to the surface of the blazed grating after the light field being collimated and expanded by the concave mirror 5, in order that the beam arrives at the whole grating surface. The quasi-collimated light incident to the grating are reflected and then are converged by the converging system of the light converging and collecting component 7 so that the light different wavelengths is converged through a converging system in the light converging and collecting component 7 and then spatially separated on the focal plane of the light converging and collecting component 7. The spectral information can be recorded by placing the point or array single-photon detector 9 on the focal plane, and the image information in the whole spectral range can be acquired by using the compressed sensing and related algorithm.

In the electric detection unit III, the input optical signals are processed into effective pulse signals by the point or array single-photon detector 9 and then are output, the number of single photons in a specific time interval is recorded through the multi-channel counter 10, and corresponding time stamps (codes) are recorded through a high-precision time measurement instrument 11 connected in parallel. Finally, the counted number of the photons, the time stamps (codes) and the random matrix output by the random number generator 8 are packaged into a data packet memory 14 of an algorithm unit V.

In the electric detection unit IV, the system control platform 13 controls the enabling of each unit component, and plays a crucial role in time-resolved measurements on the basis of the compressed sensing principle. Specifically, the system control platform 13 can maintain the corresponding random matrix of the SLM 4 unchanged in a specific time period, and can precisely control the matrix instantly change to the next random matrix at a certain moment. According to various time-resolved measurement methods, the system control platform 13 controls the light source I, the point or array single-photon detector 9, the multi-channel counter 10 and the high-precision time measurement instrument 11 to coordinate in their operations and remove asynchronous time difference among them. It shall be noted that a digital delayer 12 is introduced into the time resolution method on the basis of delay measurement to implement picosecond-level gate control of the point or array single-photon detector 9. In the time resolution method on the basis of the photon arrival time, a time to amplitude converter in the multi-channel counter 10 can record the time (start to stop) for acquiring the photons in the form of voltage into the corresponding time channels, and the photons are counted section by section according to the photon arrival time so as to obtain a plurality of accumulative values of the counts in each time interval within a period.

When the system repeats multiple times of measurement according to the compressed sensing principle, then a series of counted values, time stamps (codes) and random matrixes can be obtained, which are input to the algorithm unit V, so that the compressed sensing and related algorithm 15 in the algorithm unit V reconstructs required images according to these inputs, mainly comprising: a single-phone 2D image I (x, y), a single-photon 3D image I (x, y, z), a single-photon 2D spectral image I (x, y, $\lambda$), a single-photon time-resolved 2D image (such as fluorescence lifetime) I (x, y, t), a single-photon 3D spectral image I (x, y, z, λ), a single-photon time solved 3D image I (x, y, z, t), a single-photon time-resolved 2D spectral image I (x, y, λ, t) and a single-photon time-resolved 3D spectral image I (x, y, z, λ, t).

Figure 6:
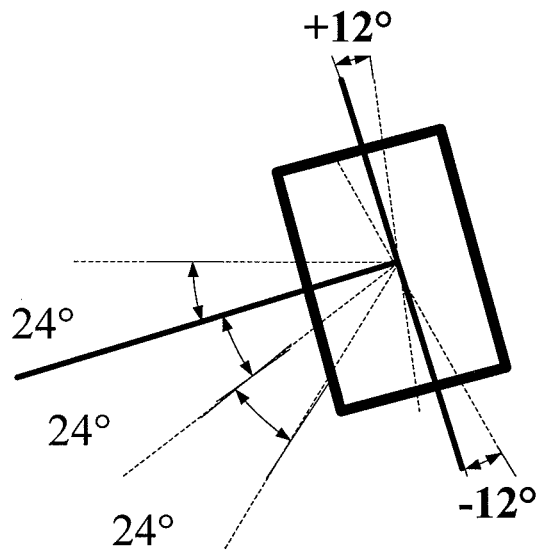
FIG. 6 shows the principle of the reflection mechanism of a single micro-mirror on a spatial light modulator of the invention when adopting a DMD.

In addition, it should be noted that a digital micro-mirror device (DMD) is used as an example of the SLM 4 to explain the reflection mechanism of a single micro-mirror, as shown in FIG. 6. When the angle between the incident light and the normal of the single micro-mirror of a micro-mirror array is of 24°, the angle between the reflected light and the normal is also of 24°; When the micro-mirror turns over +12°, the normal of the micro-mirror also turns over +12° clockwise, but the reflected light turns over +24° clockwise according to the reflection law of light, as a result, the reflected light is on the same line with the normal of the micro-mirror at the initial position. The direction of the normal of the micro-mirror at the initial position can be set as the receiving direction of the light converging and collecting component 7, thereby the emergent light finally enters into the point or array single-photon detector 9. Similarly, when the micro-mirror turns over −12°, the angle between the reflected light and the normal at the initial position form an angle of −48°, which leads to the reflected light hardly enters the subsequent light converging and collecting component, so the reflected light corresponding to −12° turnover of the micro-mirror can be ignored. Here, clockwise turnover is regarded as positive and anticlockwise turnover is regarded as negative. The receiving direction can be reversed too.

Figure 7:
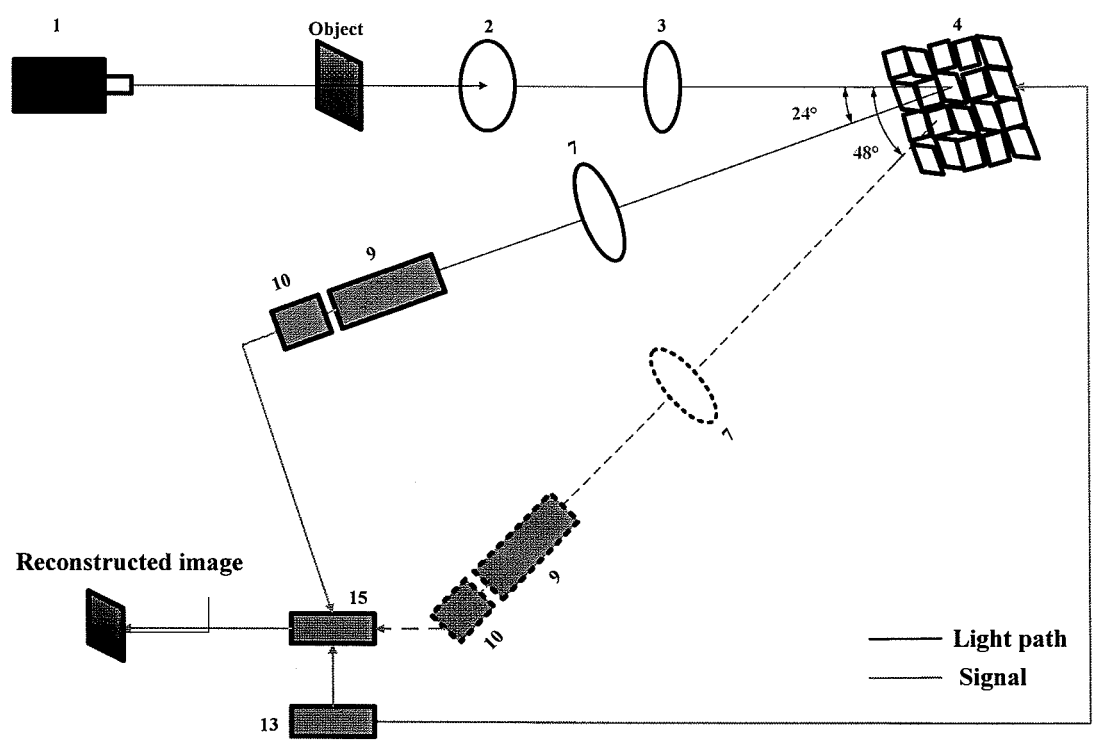
FIG. 7 shows a simplified principal diagram of a positive image and a negative image of the embodiment of the invention.

As a supplement of the above technical solution, as the simplified structural diagram of the positive image and the negative image shown in FIG. 7, the system features in that the point or array single-photon detectors 9 can be arranged both on the positive (+12 degrees) light path and the negative (−12 degrees) light path of the SLM 4 so that coincidence measurement is performed on both paths synchronously, wherein based on the co-relation between the positive (+12 degrees) random measurement matrix and the negative (−12 degrees) random measurement matrix, a correlation recovery algorithm is used so that the quality of the reconstructed images can be improved and the operating time of the recovery algorithm can be shortened.

Figure 8:
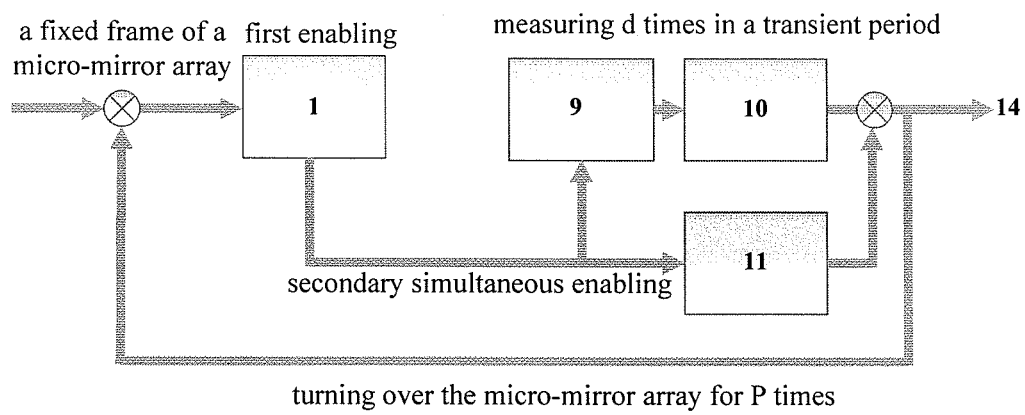
FIG. 8 is a block diagram of a time-resolved measurement method adopted in the embodiment of the invention.
Figure 9:
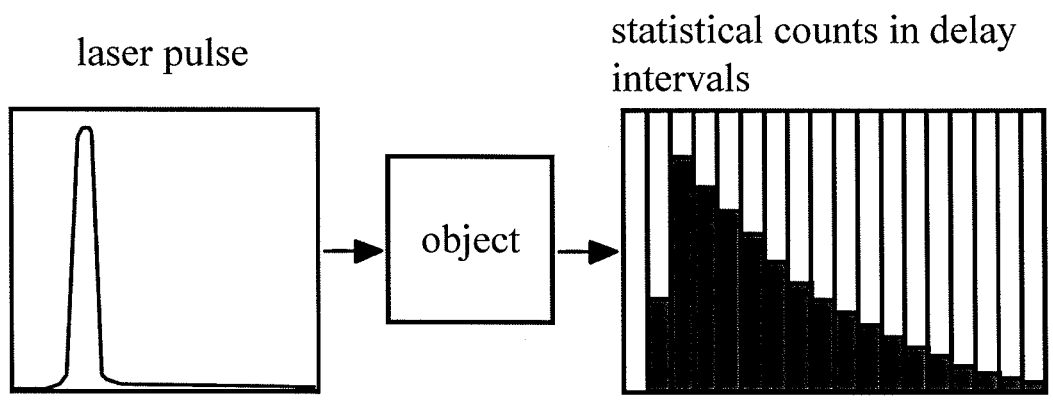
FIG. 9 is a schematic diagram showing the number of single photons being recorded at time intervals in the invention.
Figure 10:
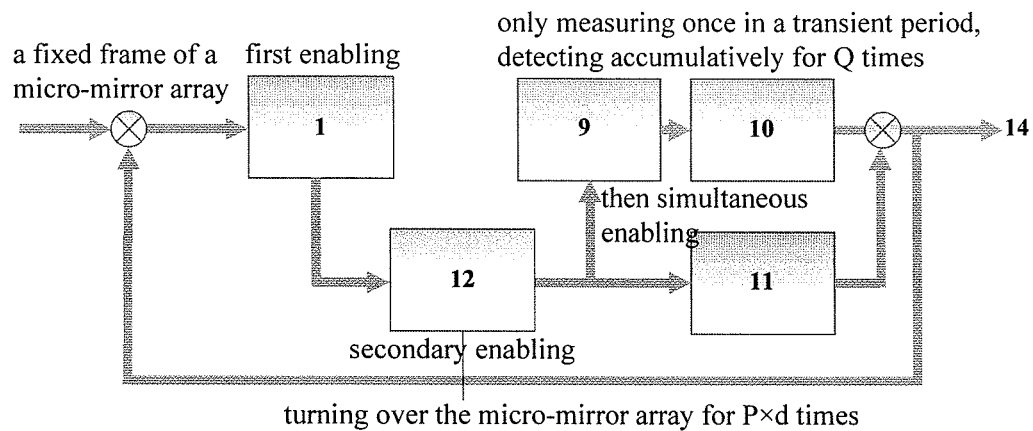
FIG. 10 is a block diagram of another time-resolved measurement method adopted in the embodiment of the invention.
Figure 11:
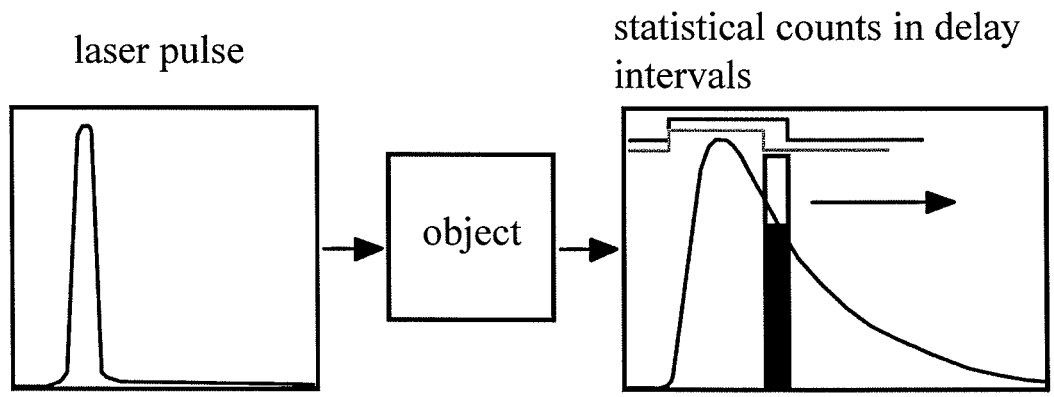
FIG. 11 is a schematic diagram of the number of single photons recorded at time sections after being applied statistical difference in the invention.

The functional block diagram of the time-resolved measurement method in the strategy I, namely the time resolution method on the basis of time interval measurement, is shown in FIG. 8, and FIG. 9 is the schematic diagram of the numbers of the single photons recorded at time intervals; the functional block diagram of the time-resolved measurement method in the strategy II, namely the time resolution method on the basis of time delay measurement, is as shown in FIG. 10, FIG. 11 is the schematic diagram of the number of the single photons recorded at a time section after being applied statistical difference, and the method is finally converted into a time resolution problem on the basis of time interval measurement; and likewise, the time-resolved measurement method in the strategy III is the time resolution method on the basis of the photon arrival time, and finally, a plurality of accumulative values in each time interval of a period as shown in FIG. 9 are obtained. The specific method has been described in detail in the summary of the invention.

As an improvement of the above technical solution, in order to analyze the signal to noise ratio (SNR for short) of the system, the SNR is supposed as the variance ratio of the signals to the system noise, wherein the system noise contains dark count of the point or array single-photon detector 9, environmental noise, electric noise, optical noise and the like. The variance can be understood as the fluctuation conditions of the signals and if the fluctuation of the system noise covers that of the signals, the compressed sensing algorithm fails; and if the fluctuation of the system noise is smaller than or far smaller than that of the signals, images can be nearly perfectly reconstructed. In order to improve the SNR of the system, preferably, the system should be packaged in a sealed case and the corresponding performance parameters of the point or array single-photon detector 9 should also be improved, after that the stability of the system will be improved, which is beneficial to improve the image quality.

In conclusion, the present time-resolved single-photon or ultra-weak light multi-D spectral imaging system is a new-generation high-performance time-resolved single-photon multi-D imaging system, which is realized on the basis of the compressed sensing (CS for short) theory and the single-photon detection technology and can effectively solve the problems caused by dimension increase. The compressed sensing principle breaks through the limit of the Nyquist/Shannon sampling theorem, and can perfectly recover the original signals in a random sampling scheme with fewer data measurements (far lower than the limit of Nyquist/Shannon sampling theorem), so the present system has better robustness. The principle of the present system mainly includes three steps: compressive sampling, sparse transform and algorithm-based reconstruction, wherein the compressive sampling is a process for mapping measured signals from high-D signals to low-D ones and collecting the resulted signals; in the sparse transform, firstly a proper $\Psi$ is selected, such that the value x', which is obtained by projecting x onto $\Psi$ transform basis, is sparse, namely x has a sparse representation under the $\Psi$ framework; and the algorithm-based reconstruction is a process for solving $y=A\Psi x'+e$ under the condition where the observation data y, the measurement matrix A and the framework $\Psi$ are known, and finally, x is retrieved from $x=\sum_{i=1}^{N} x'_i \psi_i$.

The features of the time-resolved single-photon multi-D imaging system according to the present invention lie in that the system has single-photon detection sensitivity, picosecond time resolution, nano spatial resolution and ultra-wide spectrum band, with the imaging being realized by a point detector, and so the system has the advantages of high speed, high resolution, high stability, high efficiency and high success rate of test, which is very useful for quantitative analysis in the study areas of material science, physics, chemistry, biotics and the like, for testing array-type nano material structures and biological macromolecular and cellular fine structures, and can also be applied in the scientific research fields of industrial nano semiconductor devices, biological pharmacy, batch detection and quality monitoring of clinical tumor tissues and products and the like.

The invention is a further improvement on the basis of mainly one Chinese patent titled "Single-Photon Counting Imaging System and Method" with patent number: 201110103559.3 (patentee: Center for Space Science and Applied Research, Chinese Academy of Sciences) and one Chinese patent application titled "Multi-Spectral Imaging Method for Ultra-weak Photon Emission and System Thereof". In the present invention, a spatial third-dimensional distance parameter is deduced by using the time-resolved dimension information, so it is possible to provide eight types of images: a single-phone 2D image I (x, y), a single-photon 3D image I (x, y, z), a single-photon 2D spectral image I (x, y, λ), a single-photon time-resolved 2D image (such as fluorescence lifetime) I (x, y, t), a single-photon 3D spectral image I (x, y, z, λ), a single-photon time-solved 3D image I (x, y, z, t), a single-photon time-resolved 2D spectral image I (x, y, λ, t) and a single-photon time-resolved 3D spectral image I (x, y, z, $\lambda$, t). For the first time, the invention combines the compressed sensing theory, the single-photon detection technology and the fluorescence lifetime measurement technology. In short, the invention provides a time-resolved single-photon or ultra-weak light multi-D spectral imaging system and a time-resolved single-photon or ultra-weak light multi-D spectral imaging method, belonging to the field of single-photon time-resolved imaging spectrometry. The system realizes spectral imaging measurement of an object with the capability of reflecting, scattering or transmitting, having 5D parameters information of two spatial dimensions, light intensity, time resolution and spectral resolution on ultra-weak light single-photon level by the combination of the point and array single-photon detection technology of visible light and near infrared light, the time-resolved measurement technology, the spatial light modulation technology, the compressed sensing theory, the single-photon counting imaging technology, the imaging spectrometry and the reconstruction algorithm technology. The system mainly comprises a light source, a spectral imaging measurement unit, an electrical detection unit, a system control unit and an algorithm unit, wherein the light carrying the information of the object is imaged on a spatial light modulator and is randomly modulated according to the compressed sensing theory. Then the light reflected from the modulator is collected by a point or array single-photon detector, meanwhile, the number of the photons and the arriving time of the photons are recorded. Finally, the reconstruction of the original signals is carried out using the compressed sensing algorithm and the image spectrum related algorithm. As can be seen, the present system has the advantages of single-photon detection sensitivity, high time resolution and a wide range of spectrum, and so can be widely applied in the fields of numerous new high-tech industries such as unicellular biophysics, material defect detection, nano materials, microelectronics, quantum dots, life sciences and new energy photoelectric conversion materials.

In the present invention, the photons are detected by the single-photon detector, and the number of discrete pulses output by the detector is recorded by the counter. When the time resolution technology is utilized, the time-resolved measurement method is expanded based on the time to amplitude converter (TAC for short), so the method is more suitable to be combined with the compressed sensing theory; when the compressed sensing theory is utilized, although its core algorithm is general, it is expanded to the algorithms suitable for the present invention, i.e., eight corresponding improvement solutions are proposed in respect to eight types of images, as detailed above; when the spatial light modulator is utilized, the Bernoulli binary random matrix is loaded mainly through the random number generator to realize random light modulation; and when spectral light splitting is utilized, the general light splitting technology is utilized.

Finally, it shall be noted that the algorithms in the specific implementation modes have already been proved reliable by a large quantity of experimental data, and can realize the technical solution of the invention by appropriate hardware. All the exemplary embodiments are only used for illustrating the invention, not for limitation, and can be correspondingly expanded. It shall be understood by those ordinary skilled in the art that modifications, deletions or equivalent replacements made to the technical solution of the invention do not depart from the spirit and scope of the technical solution of the invention and shall be encompassed in the scope of the claims of the invention.

The invention claimed is:

1. A time-resolved single-photon counting 2D imaging system, based on a compressed sensing principle, for obtaining an imaging spectrum by enabling an ultra-weak light source triggered by a trigger to illuminate an object, imaging the object that changes dynamically with time and outputting continuous gray level video image frames arranged according to a time sequence, comprising:

the trigger, an optical imaging system, a DMD micro-mirror array, an optical focusing and collecting system, a light attenuator, a single-photon counter, a drive control module and an optimization algorithm module;

the trigger is triggered by an ultra-weak light triggering source located at a front end of the trigger and an output end of the trigger is connected with an input end of the drive control module; when the trigger is triggered, the drive control module outputs a drive control signal to trigger the DMD micro-mirror array and the single-photon counter, connected to a first output and a second output of the drive control module, respectively, to start working; then the DMD micro-mirror array starts flipping and the single-photon counter simultaneously starts photon counting, wherein the light attenuator attenuates an intensity of light from the ultra-weak light triggering source; the optical focusing and collecting system focuses and collects the light; the single photon counter performs single-photon counting of the light;

an output end of the single-photon counter is connected with a first input end of the optimization algorithm module providing the counting result of the single-photon counter as an input parameter to the optimization algorithm module, and a second input end of the optimization algorithm module is connected with a third output of the drive control module for receiving a random measurement matrix stored by the drive control module in a selected area; the optimization algorithm module inverses a photon density image, and after M intervals of duration t, reconstructs a series of time-resolved 2D gray image video frames in time sequence;

the DMD micro-mirror array is a digital micro-mirror device;

wherein, the drive control module drives and controls turnover of the DMD micro-mirror array by downloading a pseudorandom measurement matrix, after a working area of the DMD micro-mirror array is selected, on a basis of digital light processing (DLP) technology; the DMD micro-mirror array sends a synchronous signal to the single-photon counter during turnover to ensure synchronization between the DMD micro-mirror array and the single-photon counter, wherein each time the DMD micro-mirror array turns over, the single-photon counter accumulatively accumulates a number of single photons during a time interval of the turnover; after the turnover of the DMD micro-mirror array is finished, the single-photon counter is reset to restart accumulating; all the counts and the random measurement matrix of the selected area are transmitted to the optimization algorithm module.

2. The time-resolved single-photon counting 2D imaging system according to claim 1, wherein when the system is used for color imaging, the single-photon counter is replaced by a linear array of the single-photon counters, and a spectrophotometer is arranged on a light path between the linear array of the single-photon counters and the optical focusing and collecting system.

3. The time-resolved single-photon counting 2D imaging system according to claim 1, wherein both the optical imaging system and the optical focusing and collecting system include optical lenses to perform optical imaging and optical focusing, respectively; and after ultra-weak light passes through the optical imaging system, one of isometric, reduced and enlarged images can be obtained on the DMD micro-mirror array and adjusted according to actual demands.

4. The time-resolved single-photon counting 2D imaging system according to claim 3, wherein the optical focusing and collecting system couples beams split by a spectrophotometer to a fiber by adopting fiber coupling technology, and collects the split beams at the corresponding single-photon counter separately using fiber coupling technology; and
the spectrophotometer comprises a light collimating section, a light splitting section, an angle measurement section and a luminosity observation and measurement section, and the spectrophotometer is used for spectral analysis and measurement;
wherein the spectrophotometer is a prism spectrophotometer or a grating spectrophotometer.

5. A time-resolved single-photon multi-D imaging system, which excites a fluorescence of an object through laser pulses based on a compressed sensing algorithm to obtain a light intensity distribution and imaging spectrum, realizes time resolution precision of up to a picosecond level by using a time resolution strategy, and detects transient periodic matters such as fluorescence lifetime, comprising:
a light source, a spectral imaging measurement unit, an electric detection unit, a system control unit and a processing unit;
the light source emits a laser pulse, under triggering of a trigger pulse sent by the system control unit, to an object to be measured, so the object emits fluorescence carrying information of the object;
the imaging spectrum measurement unit images light carrying the information of the object to be measured on a spatial light modulator (SLM), SLM is modulated by adopting random light and reflects the image thereon, and reflected light is collimated by a light converging and collecting component arranged on a light path and irradiated on the electric detection unit;
the electric detection unit detects the incident light according to the time resolution strategy, recording a number of photons of incident light as well as dimension information of arrival time of each photon;
the processing unit realizes spectral image reconstruction of multi-parameter information according to the input number of photons, the arrival time dimension information of the photons and random light modulation matrix information of each time period, using the compressed sensing and spectral imaging algorithm, and for outputting a plurality of different types of images;
the system control unit enables each component to synchronize pulse triggering of the light source and photon counting, and control turnover of the micro-mirror array and replacement of a random matrix on the micro-mirror array and performing corresponding adjustment before or after a transient period;
wherein, the spatial light modulator is loaded with a Bernoulli binary random matrix through a random number generator to realize random light modulation of light; the time resolution strategy adopts a frame-by-frame measurement method for a non-periodically changed long-time sequence process; an optimized time resolution strategy is adopted for a transient process with periodic change characteristic cutting a period of the transient process into a plurality of detection sub time periods, during each sub time period a point or array single-photon detector detects the object to be measured and records the number of the photons and the dimension information of arrival time of the photons, wherein each minimum time unit is used as a reconstruction object.

6. The time-resolved single-photon multi-D imaging system according to claim 5, wherein the electric detection unit further comprises:
a random number generating unit for generating a random number for modulating the spatial light modulator (SLM), processing a real random number by treating a random source in the nature as a random number source to acquire the random number and outputting the random number to the SLM;
a high-precision time interval measurement instrument for dividing a time duration of detection and recording a duration between two moments in a time coordinate system to obtain time dimension information, wherein precision can be controlled on a picosecond level;
a point or array single-photon detector, including a plurality of avalanche diodes corresponding to different wavelengths and working in a Geiger mode, for enabling some of the plurality of avalanche diodes as required, to detect arriving photons in each frame in the non-periodically changed long-time sequence process and detect arriving photons in a preset time period of each period in the transient process and output a pulse waveform, wherein the preset time period is a subset of the periodic duration;
a multi-channel counter for screening and accumulating a number of peaks of the pulse waveform and recording the number of photons and the arrival time of the photon detected by each channel of the point or array single-photon detector;
a delayer for sending control signals for laser pulse in a certain transient period and sending enabling gate control signals to the point or array single-photon detector or the high-precision time measurement instrument or delaying a gate width rising edge for a certain time period for sending, the delayed time period capable of being used as a detection time sub period of the point and single-photon detector in the corresponding transient period, and the time resolution precision being 20 ps.

7. The time-resolved single-photon multi-D imaging system according to claim 6, wherein the delayer is a time length division module for equally dividing the transient period into a plurality of sub periods, each sub period is a time unit for detection and counting of photons for the point or array single-photon detector and the multi-channel counter, wherein the time resolution precision is 50 ps.

8. The time-resolved single-photon multi-D imaging system according to claim 6, wherein one of the time length division module and the delayer is a time/amplitude converter arranged in the multi-channel counter, wherein the time/amplitude converter converts the arrival time of the photons into a voltage, records the voltage in the corresponding channels, divides the photon numbers according to the arrival time of the photons into several sections and obtains the photon numbers of each of the multiple sections within one period, wherein the time resolution precision is 5 ps.

9. The time-resolved single-photon multi-D imaging system according to claim 5, further comprising a grating light splitting component arranged on a light path between the light converging and collecting component and the point or array single-photon detector, the grating light splitting component collimates incident light into collimated light using a concave mirror before splitting the light and collimates the light of each wavelength using a lens to converge the light to the avalanche diodes in corresponding channels acquiring dimension information about the spectrum including light intensity information in each wavelength, the dimension information about the spectrum is used for reconstructing an image containing the wavelength parameters of the spectrum;

wherein the point or array single-photon detector is arranged on the focal plane of the grating light splitting component.

10. The time-resolved single-photon multi-D imaging system according to claim 5, further comprising:

a data read/write memory for storing each input sub time period, the number of photons in each frame or each enabling gate control signal time period, the dimension information of arrival time of each photon, the corresponding random matrix and the wavelength information corresponding to each channel of the detector;

an algorithm processing unit for reconstructing images on the basis of the input counting values of the multi-channel counter, the random matrix controlling a spatial light modulator-demodulator, the time dimension information recorded by the delayer or the time length division module or the time/amplitude converter, and the wavelength information corresponding to each channel of the detector, and outputting the following types of images:

(1) a single-phone 2D image I (x, y), wherein when the single-phone 2D image I (x, y) is to be output, the algorithm processing unit reconstructs the image according to the input counting value and the random matrix parameters by adopting different sparse frameworks for different types of images and adopting the compressed sensing algorithm, and performs post processing on the image by combining the matrix completion theory, wherein the compressed sensing algorithm includes a greedy reconstruction algorithm, a matching pursuit (MP) algorithm, an orthogonal matching pursuit (OMP) algorithm, a base pursuit (BP) algorithm, LASSO, LARS, GPSR, a Bayesian estimation algorithm, magic, IST, TV, StOMP, CoSaMP, LBI, SP, 11_ls, a smp algorithm, a SpaRSA algorithm, a TwIST algorithm, a 10 reconstruction algorithm, a 11 reconstruction algorithm, and a 12 reconstruction algorithm and the like;

(2) a single-photon 2D spectral image I (x, y, λ), wherein when the single-photon 2D spectral image I (x, y, λ) is to be output, the algorithm processing unit is further provided with the wavelength information corresponding to each channel of the detector on the basis of (1) to obtain a light intensity spatial distribution image in each wavelength for an imaging spectrometer, and color imaging is realized using the light intensity spatial distribution under three primary color;

(3) a single-photon time-resolved 2D image, wherein when a single-photon time-resolved 2D image is to be output, the algorithm processing unit is further provided with the dimension information of arrival time of the photons on the basis of (1) to reconstruct the image of an object in each sub period, thereby recovering the dynamic changing process of the image within the full time length;

(4) a single-photon time-resolved 2D spectral image I (x, y, λ, t), wherein when a single-photon time-resolved 2D spectral image I (x, y, λ, t) is to be output, the algorithm processing unit is further provided with the dimension information of arrival time of the photons on the basis of (2) to reconstruct the image of the object in each wavelength of the light within each sub period;

(5) a single-photon 3D image I (x, y, z), wherein when a single-photon 3D image I (x, y, z) is to be output, for an object with large-scale time sequence and without exciting fluorescence, the algorithm processing unit further calculates an optical path difference of spatial positions, namely spatial third-dimensional distance information using an interval between the arrival time of the photons on the basis of (3), the optical path difference is a derivative and a subset of time-resolved dimension, thereby obtaining a plurality of layers of image frames corresponding to different spatial distances;

(6) a single-photon 3D spectral image I (x, y, z, λ,), wherein when a single-photon 3D spectral image I (x, y, z, λ) is to be output, the algorithm processing unit is further provided with the wavelength information corresponding to each channel of the detector on the basis of (5) to obtain light intensity spatial 3D distribution in each wavelength;

(7) a single-photon time solved 3D image I (x, y, z, t), wherein when a single-photon time solved 3D image I (x, y, z, t) is to be output, the algorithm processing unit identifies and distinguishes the large-scale spatial third-dimensional distance information and the dimension information of the sub periods of a transient period on the basis of (5) to reconstruct the time-resolved 3D image of the object, wherein the time length of the former is greater than that of the latter; and (8) a single-photon time-resolved 3D spectral image I (x, y, z, λ, t), wherein when a single-photon time-resolved 3D spectral image I (x, y, z, λ, t) is to be output, the algorithm processing unit identifies and distinguishes the large-scale spatial third-dimensional distance information and the dimension information of the sub periods of a transient period on the basis of (6), so as to obtain a time-resolved 3D spectral image.

11. A time-resolved single-photon multi-D imaging method, comprising:

imaging light released, reflected, scattered, transmitted or refracted from an object by being excited or self-exciting on a spatial light modulator through a lens set under a condition of ultra-weak light single photons;

setting a random modulation base matrix on the spatial light modulator according to a compressed sensing algorithm, collecting the reflected light of the spatial light modulator to a point or array single-photon detector; implementing reconstruction of a spectral image with 5D parameter information by adopting a time-resolved strategy through the compressed sensing algorithm and a spectral imaging algorithm, realizing a single-photon time-resolved spectral image on a nano scale and a picosecond scale;

wherein the time-resolved strategy can adopt any one of:

Strategy I: a period of the transient process is 1.5 ms to 5 ms, a light source is turned on, wherein the transient period is marked as T, when T is equally divided into d time intervals, those intervals are marked as $t_1, t_2, t_3, \ldots t_d$ respectively, and during T, a random modulation base matrix on the spatial light modulator is kept constant; the point or array single-photon detector detects single photons within a time interval $t_i$, where i=1, 2, . . . d, and a multi-channel counter records a number of the single photons within each time interval, counts of single photons are combined with time codes recorded by a high-precision time measurement instrument to form a data packet to obtain the time interval corresponding to each count; before a next laser pulse is emitted at a moment when a sampling of d time intervals of period T is finished, the spatial light modulator instantly turns over to a next frame to carry out a whole set of operations as above; then the spatial light modulator repeats turnovers for P times so that each time interval $t_i$ has a corresponding number of P counts corresponding to P random matrixes, respectively; by performing algorithm-based reconstruction on these d time intervals, respectively, according to a one-to-one correspondence relationship, a changing process of the spectral intensity within a transient period can be retrieved; if the light intensity is ultra-weak, by performing measurement and accumulation multiple times, the corresponding counts are increased, and then performing algorithm-based reconstruction on the d time intervals, respectively, according to the one-to-one correspondence relationship, the changing process of the spectral intensity within a transient period can be retrieved;

Strategy II: a period of the transient process is 80 ns to 1.5 ms, at a same time when a trigger pulse is sent to a light source, an enabling control signal is also sent to each component of the system, wherein the enabling control signal passes through a delayer before arriving at the point or array single-photon detector and the high-precision time measurement instrument; 1) keeping a fixed frame of the spatial light modulator unchanged, keeping a start end of a gate width of the point or array single-photon detector in coincidence with a starting moment of the transient period, the point or array single-photon detector and the high-precision time measurement instrument simultaneously start measurements and only make the measurement once within the period T, wherein the gate width is smaller than the transient period T, to obtain a counted number which is a number of single photons in an overlapping time period of the gate width and the transient period; by repeating the above procedure 1) for Q times and summing up the counts of every time of the Q times repeated the measurements obtaining a first sum; then the gate width is increased by 20 ps using a digital delayer; by performing 1) above Q times, a second sum is obtained, the first sum is regarded as a reference value and a difference between the first sum and the second sum is a statistic counted number within the delayed gate width, the statistical counted number of d sections is obtained from a reference moment to an end moment of the fluorescence light; 2) if the gate width is kept unchanged but the arrival moment of the gate width is shifted to an earlier moment, similarly, a series of statistical counted numbers of d sections between a fluorescence lifetime starting moment and the reference moment could be obtained; next, the spatial light modulator is turned over once to carry out the above; repeating P times of turnover of the spatial light modulator so that each time interval $t_i$ has P counted numbers corresponding to P random matrixes, respectively; based on a one-to-one correspondence relationship between the P counted numbers and the P random matrixes the transient process of an image is reconstructed within a period by performing algorithm-based reconstruction on the d time intervals, if the light intensity is ultra-weak, multiple times of measurements and accumulations are performed multiple times to increase corresponding P counted numbers and the P random matrixes; and Strategy III: keeping a fixed frame of the spatial light modulator unchanged, taking a trigger pulse sent to the light source as a reference pulse of a time to amplitude converter, then a time to amplitude recording the arrival time of the photons in a form of voltage into a corresponding time channel; dividing the photon numbers into multiple sections according to the arrival time of the photons; and obtaining a series of statistical counts of d sections within one period; turning over the spatial light modulator once to carry out the above; repeating P times of turnover of the spatial light modulator so that each time interval $t_i$ has corresponding P counts corresponding to P random matrixes respectively; based on the one-to-one correspondence relationship between the P counts and the P random matrixes reconstructing the transient process of an image within a period by performing algorithm-based reconstruction on the d time intervals, if the light intensity is ultra-weak, performing multiple measurements and accumulations to increase corresponding P counted numbers and the P random matrixes.

12. The time-resolved single-photon multi-D imaging method according to claim 11, wherein, the spatial light modulator is a micro-mirror array;

the single-photon detector is one of a photoelectric multiplier, an intensified charge coupled device ICCD, an electron multiplying charge coupled device EMCCD and a linear mode or Geiger mode single-photon detector; and the light source emits infrared or visible light, and the laser is one of a femtosecond and a nanosecond pulse laser with proper wavelength.

* * * * *